United States Patent
Chen et al.

(10) Patent No.: US 11,555,043 B2
(45) Date of Patent: Jan. 17, 2023

(54) PREPARATION METHOD FOR NANO ORGANOMETALLIC CARBOXYLATE

(71) Applicant: CHANGZHOU UNIVERSITY, Changzhou (CN)

(72) Inventors: Qun Chen, Changzhou (CN); Haiqun Chen, Changzhou (CN); Guangyu He, Changzhou (CN); Jian Lu, Changzhou (CN); Mingyang He, Changzhou (CN); Chunping Fang, Changzhou (CN); Shuhua Wang, Changzhou (CN); Wen Yi, Changzhou (CN); Lina Zhang, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 17/432,941

(22) PCT Filed: Jul. 31, 2019

(86) PCT No.: PCT/CN2019/098581
§ 371 (c)(1),
(2) Date: Mar. 31, 2022

(87) PCT Pub. No.: WO2020/258441
PCT Pub. Date: Dec. 30, 2020

(65) Prior Publication Data
US 2022/0267355 A1    Aug. 25, 2022

(30) Foreign Application Priority Data
Jun. 28, 2019   (CN) .......................... 201910574188.3

(51) Int. Cl.
*C01F 3/00* (2006.01)
*C07F 3/06* (2006.01)
(Continued)

(52) U.S. Cl.
CPC .................. *C07F 3/06* (2013.01); *C07F 1/04* (2013.01); *C07F 3/003* (2013.01); *C07F 3/02* (2013.01)

(58) Field of Classification Search
CPC ........................................................ C07F 3/06
(Continued)

(56) References Cited

FOREIGN PATENT DOCUMENTS

| CN | 102583813 A | 7/2012 |
|---|---|---|
| CN | 102633617 A | 8/2012 |

(Continued)

OTHER PUBLICATIONS

English translation of CN 102583813 A obtained from ESPACENET on Jul. 18, 2022. (Year: 2022).*

(Continued)

*Primary Examiner* — Christine T Mui
*Assistant Examiner* — Emily R. Berkeley
(74) *Attorney, Agent, or Firm* — Idea Intellectual Limited; Margaret A. Burke; Sam T. Yip

(57) ABSTRACT

Provided in the present invention is a preparation method for a nano organometallic carboxylate which effectively solves the problems of a complex washing process, and cumbersome, dangerous and uneconomical preparation of lye in traditional methods for producing organometallic carboxylates. A new method for preparing high-quality organometallic carboxylates by using a carboxylic acid, caustic soda, a metal oxide or a hydroxide as starting materials, and using ball milling to assist reaction thereof. The present invention not only efficiently utilizes lye, it also obtains high-quality organometallic carboxylates, which overcomes the technical prejudice that the prior art uses calcium chloride, sodium chloride and other salts for poor reaction efficiency. The problem in environmental pollution caused by the washing waste liquid in the existing process is fundamentally solved. At the same time, addition of non-ionic surfactants makes ball milling more efficient and significantly reduces the particle size of the product.

4 Claims, 1 Drawing Sheet

(51) Int. Cl.
  *C07F 1/04*  (2006.01)
  *C07F 3/00*  (2006.01)
  *C07F 3/02*  (2006.01)

(58) Field of Classification Search
  USPC ........................................................ 526/493
  See application file for complete search history.

(56) References Cited

FOREIGN PATENT DOCUMENTS

| | | |
|---|---|---|
| CN | 103173845 A | 6/2013 |
| CN | 103820860 A | 5/2014 |
| CN | 104292100 A | 1/2015 |
| CN | 105967999 A | 9/2016 |
| CN | 106119970 A | 11/2016 |
| JP | 2005047877 A | 2/2005 |

OTHER PUBLICATIONS

Pei Kang Shen; Chemistry for Materials; Sun Yat-sen University Press; May 2012; pp. 249-250.
1st Office Action of corresponding China patent application No. 201910574188.3 dated Dec. 26, 2019.

\* cited by examiner

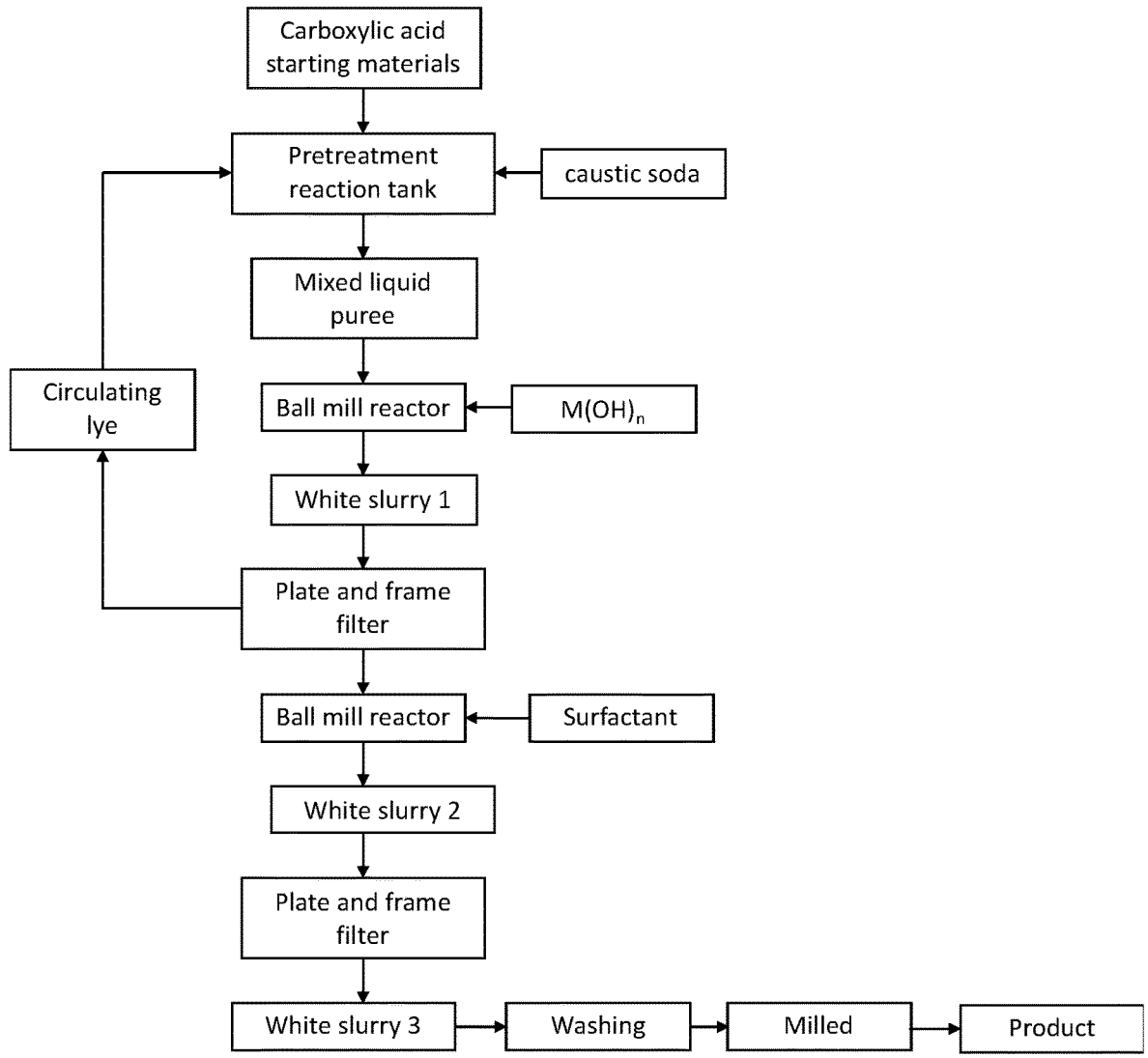

PREPARATION METHOD FOR NANO ORGANOMETALLIC CARBOXYLATE

FIELD OF THE INVENTION

The present invention belongs to the technical field of organometallic carboxylate preparation, and specifically relates to a preparation method of nano organometallic carboxylate.

BACKGROUND OF THE INVENTION

The traditional method of preparing metal carboxylates is based on the following reversible reaction:

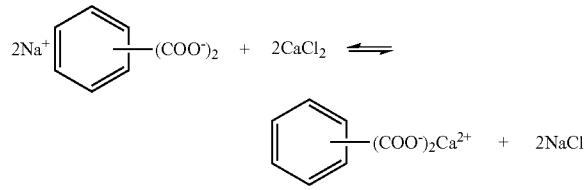

At present, preparation of calcium carboxylate by traditional methods is basically outdated or even eliminated. It can be seen from the above reaction formula that the main problems of the traditional methods include: during preparation, both $CaCl_2$ and $NaCl$ are water-soluble salts, and the conversion rate of materials in the corresponding reaction is pretty low. Even worse by using the traditional methods is that the waste residue produced by the reaction contains a large number of raw materials and products, resulting in a low yield of the product. In terms of the product, the washing process is a complex and cumbersome process, and this is the key to success of the reaction. In the traditional methods of producing metal organic carboxylates, the water washing process is complex; the preparation of alkali liquor is cumbersome, dangerous and uneconomical.

SUMMARY OF THE INVENTION

The purpose of this section is to outline some aspects of the embodiments of the present invention and briefly introduce some preferred embodiments. Some simplifications or omissions may be made in this part, the description, abstract and the title of the invention in this application to avoid obscuring the purpose of this part, the description, abstract and the title of the invention, and such simplifications or omissions cannot be used to limit the scope of the present invention.

In view of the above technical defects, the present invention is provided.

Therefore, as one aspect of the present invention, the present invention overcomes the deficiencies in the prior art and provides a method for preparing nano organometallic carboxylate.

In order to solve the above technical problems, the present invention provides the following technical solutions. A method for preparing nano organometallic carboxylate includes:
using

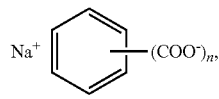

metal hydroxides or metal oxides as starting materials to react, with one or more nonionic surfactants to prepare organometallic carboxylates, where n=1 or 2.

The metal hydroxides are less alkaline than NaOH and the solubility thereof in water is lower than NaOH.

The metal oxides can react with water and the alkalinity of the generated hydroxide is lower than that of NaOH.

In an embodiment of the preparation method of nano organometallic carboxylate according to the present invention, the metal hydroxides include calcium hydroxide, magnesium hydroxide, and zinc hydroxide; the metal oxides include calcium oxide, magnesium oxide, and zinc oxide.

In an embodiment of the preparation method of nano organometallic carboxylate according to the present invention, the nonionic surfactant include one or more of alkylphenol polyoxyethylene ether, sorbitan monooleate, and fatty alcohol polyoxyethylene ether; the dosage of the nonionic surfactants is controlled at 0.1%~1% of the total mass of the reaction raw materials.

In an embodiment of the preparation method of nano organometallic carboxylate according to the present invention, the molar ratio of

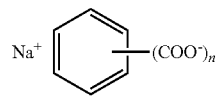

to the metal hydroxides or metal oxides is 1:0.5 to 0.55.

In an embodiment of the preparation method of nano organometallic carboxylate according to the present invention, the method further includes ball milling during the reacting of

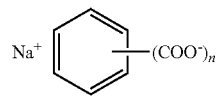

with the metal hydroxides or metal oxides.

In an embodiment of the preparation method of nano organometallic carboxylate according to the present invention, the frequency of ball milling is 30~100 Hz and the time duration thereof is 120~300 min.

In an embodiment of the preparation method of nano organometallic carboxylate according to the present invention, the method further includes using

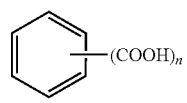

and NaOH as raw materials to prepare

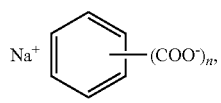

where n=1 or 2.

In an embodiment of the preparation method of nano organometallic carboxylate according to the present invention, the molar ratio of

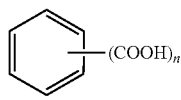

to NaOH is 1:1~1.2.

In an embodiment of the preparation method of nano organometallic carboxylate according to the present invention, the method further includes controlling the reaction process such that the mass concentration of NaOH is 5% to 15%.

In an embodiment of the preparation method of nano organometallic carboxylate according to the present invention, the prepared organometallic carboxylate has an average particle size of 10-50 microns; the NaOH is recycled during the preparation, where the amount of NaOH supplemented in each cycle of reaction is according to the molar ratio between

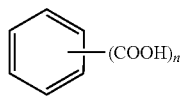

and NaOH in 1:0.05-0.2.

Beneficial effects of the present invention include: to effectively solve the problems of complicated water washing process, and avoid the complicated, dangerous and uneconomical lye preparation process in the traditional production process of metal organic carboxylates, a new method for preparing high-quality organometallic carboxylates by using carboxylic acid, caustic soda, metal oxides or hydroxides as raw materials and using ball milling to assist the reaction is provided. Compared with the traditional production process, the present invention not only efficiently utilizes lye, it also obtains high-quality organometallic carboxylates, which overcomes the technical prejudice that the prior art uses calcium chloride, sodium chloride and other salts for poor reaction efficiency. The problem in environmental pollution caused by the washing waste liquid in the existing process is fundamentally solved. At the same time, addition of non-ionic surfactants makes ball milling more efficient and significantly reduces the particle size of the product. The present invention can bring more environmental benefits and economic benefits.

BRIEF DESCRIPTION OF THE DRAWINGS

In order to explain the technical solutions of the embodiments of the present invention more clearly, the following will briefly introduce the drawings used in the detailed description of the embodiments. Obviously, the drawings in the following description are only some embodiments of the present invention. For those of ordinary skill in the art, other drawings can be obtained from these drawings without creative effort, which includes:

FIG. 1 is a process flow diagram depicting preparation of ultrafine organometallic carboxylates according to the present invention, where the recycled lye is used for pretreatment reaction.

DETAILED DESCRIPTION

In order to make the above-mentioned objects, features and advantages of the present invention more obvious and understandable, the specific embodiments of the present invention will be described in detail below in conjunction with specific embodiments.

In the following description, many specific details are explained in order to fully understand the present invention, but the present invention can also be implemented in other ways different from those described here. Those skilled in the art can make similar promotion without violating the connotation of the present invention. Therefore, the present invention is not limited by the specific embodiments disclosed below.

In addition, the "one embodiment" or "embodiment" referred to herein refers to a specific feature, structure, or characteristic that can be included in at least one implementation of the present invention. The appearances of "in one embodiment" in different places in this specification do not all refer to the same embodiment, nor are they separate or selectively mutually exclusive embodiments with other embodiments.

The synthesis scheme of preparing the nano-organometallic carboxylate according to the present invention is:

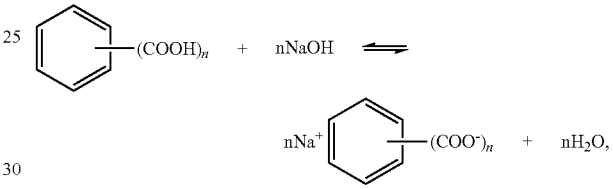

wherein, n=1 or 2,

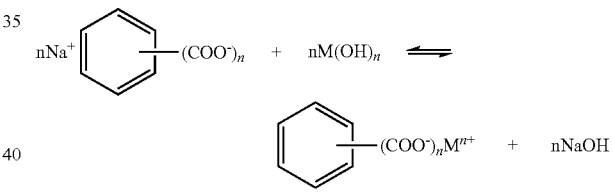

wherein, n=1 or 2, $M(OH)_n$ is a metal hydroxide having a pH value less than pH=10 and a solubility less than that of NaOH in water at 25° C., where M is preferably Ca, Mg, Zn; or:

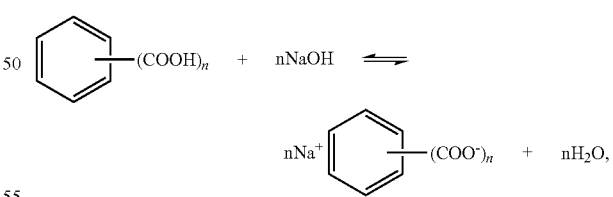

wherein, n=1 or 2,

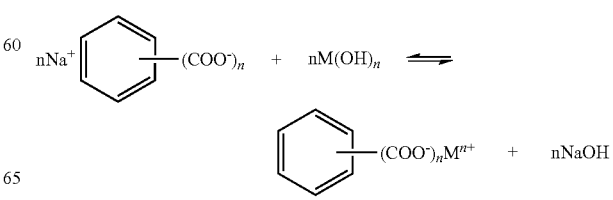

wherein, n=1 or 2, where M is preferably Ca, Mg, Zn.

In one example,

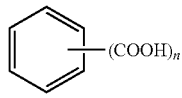

(where n=1, 2, referred to as carboxylic acid) is prereacted with caustic soda in the reactor, the molar ratio of carboxylic acid to caustic soda is controlled at 1:1~1.2, and recycled lye is added to fully react the carboxylic acid with caustic soda. A mixed solution obtained from the afore-mentioned reaction, a certain amount of washing water and metal hydroxides are added into a blender, and after being blended evenly, the reaction mixture is added to a ball mill, and the ball mill reactor is initiated. The frequency of the ball mill is controlled at 30~100 Hz, and the time duration of ball milling is controlled at 120~300 min. The amount of water is determined according to the required concentration of lye, and the concentration of lye is 5-15%. After completion of each reaction cycle, only a small amount of caustic soda needs to be added for each subsequent reaction (the molar ratio of carboxylic acid to caustic soda is 1:0.05~0.2). After the reaction is completed, the reaction product is filtered when it is still hot, and washed with water. The lye obtained after filtering is concentrated, and re-added into the reactor through circulation to react with carboxylic acid. The solid obtained after filtration is added to the ball mill again, and one or more non-ionic surfactants is/are added (the amount is controlled at 0.1% to 1% to the total mass of the raw materials); the frequency of the ball mill is controlled at 30-100 Hz; and the time duration of ball milling is controlled at 120-300 min. After the reaction is over, the reaction product is filtered when it is still hot, and washed with water. During the washing process, water is constantly added until the pH value reaches 6 to 10 as the end point. After the reaction is finished, press filtration or continuous centrifugation while the hot plate and frame are used, and the washing water is collected and added to the ball mill. The solid is dried, crushed, and sieved to obtain ultrafine organometallic carboxylates.

Under certain conditions (that is, under certain concentration and certain temperature), the reaction described hereinabove will establish an equilibrium, but cannot reach the end point. Because caustic soda is easily soluble in water, during the preparation process, the direction of the synthesis scheme mainly depends on the solubility of the resulting organometallic carboxylates. As the reaction progresses, the NaOH content increases, and due to the common ion effect, the solubility of $M(OH)_n$ decreases until it approaches the solubility of the organometallic carboxylate and establishes an equilibrium.

Preferably, during the research and development process, it is found that by adding a ball milling reactor to carry out the ball milling reaction, the reaction can be better promoted, and homogenous particles of ultrafine organometallic carboxylates can be obtained. Through further separation, the organometallic carboxylates obtained are washed, neutralized and washed in the same reactor, and the mother solution is reused, which can not only increase the yield of lye, but also further obtain high-quality ultrafine organometallic carboxylates.

The invention reacts carboxylic acid with quicklime or slaked lime under optimized process and manufacturing conditions, and can obtain high-yield lye through an effective separation means. The addition of non-ionic surfactant makes ball milling more efficient and reduces product particle size, in order to obtain high-purity ultra-fine organometallic carboxylates with an average particle size of 10-50 microns. A large number of studies on applications thereof show that the ultrafine organometallic carboxylates can be widely used in water-based coatings, plastics, rubber, papermaking and other fields, with excellent performances.

Example 1

In this example, the starting materials are terephthalic acid, caustic soda, slaked lime and non-ionic surfactant, such as sorbitan monooleate (SPAN 80 ®). The total concentration of circulating lye is 82.5 g/L (calculated based on NaOH). The amount of initial caustic soda added is calculated according to the molar ratio of terephthalic acid to caustic soda of 1:2.3 in terms of their chemical reaction quantitative measurement, and the amount of non-ionic surfactant is 0.5% of the total mass of the starting materials. After the initial reaction is completed, the solid-liquid separation is carried out, and the filtrate after separation is transferred to a ball mill. The amount added is calculated according to the molar ratio during the reaction between sodium terephthalate and slaked lime (purity 82%) in 1:0.88. The main reaction process is carried out at a ball mill frequency of 60 Hz and the reaction time is 180 min in order to obtain a white slurry 1. After the main reaction is completed, the system is filtered again to separate the solid from the liquid. The filtered white slurry 1 is added to the ball mill again, followed by adding the non-ionic surfactant, sorbitan monooleate (SPAN 80®), and water for reaction. The main reaction is carried out at a ball mill frequency of 60 Hz for a reaction time of 60 min to obtain a white slurry 2. After the reaction is completed, it is washed with hot water and then milled to obtain ultrafine calcium terephthalate. The concentration of the filtrate is measured. When the concentration of the filtrate reaches the concentration of circulating lye NaOH at 82.5 g/L, the circulating lye NaOH is added to the pretreatment tank again for the next round of pretreatment reaction (the process is shown in FIG. 1).

The purity of white slurry 2 is 94.6%, the yield is ≥99%, and the average particle size is 40 nm.

The non-ionic surfactant, such as sorbitan monooleate (SPAN 80®), makes ball milling more efficient and reduces the particle size of the product.

Example 2

In this example, the starting materials are terephthalic acid, caustic soda, slaked lime and TX-10 (belonging to alkylphenol polyoxyethylene ethers). The total concentration of circulating lye is 87.6 g/L (calculated based on NaOH). The amont of initial caustic soda added is calculated according to the molar ratio of terephthalic acid to caustic soda of 1:2.3 in terms of their chemical reaction quantitative measurement, and the amount of non-ionic surfactant is 0.4% of the total mass of starting materials. After the initial reaction is completed, the solid-liquid separation is carried out, and the filtrate after separation is transferred to the ball mill. The amount added is calculated according to the molar ratio during the reaction between sodium terephthalate and slaked lime (purity 80%) in 1:0.88. The main reaction process is carried out at the ball mill frequency of 60 Hz and the reaction time is 180 min in order to obtain a white slurry 1. After the main reaction is completed, the system is filtered again to separate the solid from the liquid. The filtered white slurry 1 is added to the ball mill again, following by adding TX-10 and water for reaction. The main reaction process is carried out at a ball mill frequency of 60 Hz for a reaction time of 60 min to obtain white slurry 2. After the reaction is completed, it is washed with hot water and then milled to obtain ultrafine calcium terephthalate. The concentration of the filtrate is measured. When the concentration of the filtrate reaches the concentration of circulating lye NaOH at 87.6 g/L, the circulating lye NaOH is added to the pretreatment tank again for the next round of pretreatment reaction (the process is shown in FIG. 1).

The purity of white slurry 2 is 95.3%, the yield is ≥99%, and the average particle size is 30 nm.

Example 3

In this example, the starting materials are terephthalic acid, caustic soda, quick lime, and AE-09 (belonging to fatty alcohol polyoxyethylene ethers). The total concentration of circulating lye is 78.5 g/L (calculated based on NaOH). The amount of initial caustic soda added is calculated according to the molar ratio of terephthalic acid to caustic soda of 1:2.3 in terms of their chemical reaction quantitative measurement, and the amount of non-ionic surfactant is 0.5% of the total mass of the staring materials. After the initial reaction is completed, the solid-liquid separation is carried out, and the filtrate after separation is transferred to the ball mill. The amount added is calculated according to the molar ratio during the reaction between sodium terephthalate and slaked lime (purity 75%) in 1:0.88. The main reaction process is carried out at the ball mill frequency of 60 Hz and the reaction time is 180 min in order to obtain a white slurry 1. After the main reaction is completed, the system is filtered again to separate the solid from the liquid. The filtered white slurry 1 is added to the ball mill again, followed by adding AE-09 and water for reaction. The main reaction is carried out at a ball mill frequency of 60 Hz for a reaction time of 60 min to obtain a white slurry 2. After the reaction is completed, it is washed with hot water and then milled to obtain ultrafine calcium terephthalate. The concentration of the filtrate is measured. When the concentration of the filtrate reaches the concentration of circulating lye NaOH at 78.5 g/L, the circulating lye NaOH is added to the pretreatment tank again for the next round of pretreatment reaction (the process is shown in FIG. 1).

The purity of white slurry 2 is 95.7%, the yield is ≥99%, and the average particle size is 20 nm.

Example 4

In this example, the starting materials are terephthalic acid, caustic soda, magnesium hydroxide and non-ionic surfactants, including fatty alcohol polyoxyethylene ethers (AE-09) and sorbitan monooleate (SPAN 80®). The total concentration of circulating lye is 81.9 g/L (calculated based on NaOH). The amount of initial caustic soda added is calculated according to the molar ratio of terephthalic acid to caustic soda of 1:2.3 in terms of their chemical reaction quantitative measurement, and the amount of non-ionic surfactant is 0.5% of the total mass of the stating materials. After the initial reaction is completed, the solid-liquid separation is carried out, and the filtrate after separation is transferred to a ball mill. The amount added is calculated according to the molar ratio during the reaction between sodium terephthalate and magnesium hydroxide (purity 93%) in 1:0.88. The main reaction process is carried out at a ball mill frequency of 60 Hz and the reaction time is 180 min in order to obtain a white slurry 1. After the main reaction is completed, the system is filtered again to separate the solid from the liquid. The filtered white slurry 1 is added to the ball mill again, followed by adding non-ionic surfactants, including fatty alcohol polyoxyethylene ethers (AE-09 and sorbitan monooleate (SPAN 80®), Span 80 and water for reaction. The main reaction process is carried out at a ball mill frequency of 60 Hz for a reaction time of 60 min to obtain a white slurry 2. After the reaction is completed, it is washed with hot water and then milled to obtain ultrafine magnesium terephthalate. The concentration of the filtrate is measured. When the concentration the filtrate reaches the concentration of circulating lye NaOH at 81.9 g/L, the circulating lye NaOH is added to the pretreatment tank again for the next round of pretreatment reaction (the process is shown in FIG. 1).

The purity of white slurry 2 is 93.6%, the yield is ≥99%, and the average particle size is 40 nm.

Example 5 (Control Example)

In this example, the starting materials are benzoic acid, caustic soda and calcium chloride. The total salt concentration in the washing water is 28.7 g/L (calculated based on NaCl), and the purity of calcium chloride used in the starting reaction is 91%. The amount of initial caustic soda added is calculated according to the molar ratio of benzoic acid to caustic soda of 1:2.2 in terms of their chemical reaction quantitative measurement. After the initial reaction is completed, solid-liquid separation is carried out, and the filtrate after separation is transferred to the reaction tank. The amount added is calculated according to the the molar ratio during the reaction between sodium benzoate and quicklime in 1:0.9. Control the stiffing frequency in the reaction tank to carry out the main reaction process at 120 r/min, the reaction time is 90 min, and obtained white slurry 1. After the main reaction is completed, the system is filtered again to separate the solid from the liquid. The filtered white slurry 2 is fully washed with hot water, and then then milled to obtain calcium benzoate. The concentration of the filtrate is measured, and after sufficient dilution, post-processing is performed (the process is shown in FIG. 1).

The purity of white slurry 2 is 88.6% and the yield is less than 90%.

The present invention effectively solves the problems of complex water washing process, complicated lye preparation, dangerous and uneconomical in the traditional production process of metal organic carboxylate, and proposes a kind of carboxylic acid, caustic soda, metal oxide or hydroxide as raw materials, the use of ball milling method to assist the reaction, a new technology for preparing high-quality organometallic carboxylates. Compared with the traditional production process, the present invention can obtain high-quality organometallic carboxylates in addition to the efficient use of lye, which overcomes the technical prejudice that the prior art uses calcium chloride, sodium chloride and other salts for poor reaction efficiency. The problem of environmental pollution caused by the washing waste liquid in the existing process is fundamentally solved.

It should be noted that the above embodiments are only used to illustrate the technical solutions of the present invention and not to limit them, although the present invention has been described in detail with reference to the preferred embodiments. Those of ordinary skill in the art should understand that modifications or equivalent substitutions can be made to the technical solutions of the present invention without departing from the spirit and scope of the technical solutions of the present invention, which should all be covered by the scope of the claims of the present invention.

What is claimed is:

1. A method for preparing nano organometallic carboxylates, comprising:

using

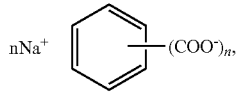

metal hydroxides and/or metal oxides as starting materials to react with one or more nonionic surfactants to prepare organometallic carboxylates, wherein n=1 or 2; wherein the nonionic surfactants comprise one or more of alkylphenol polyoxyethylene ether, sorbitan monooleate, and fatty alcohol polyoxyethylene ether; the concentration of the nonionic surfactants is controlled at 0.1%~1% of the total mass of the starting material; wherein the molar ratio of

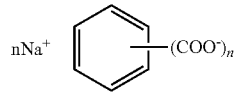

to the metal hydroxides or metal oxides is 1:0.5-0.55, wherein

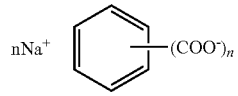

reacting with the metal hydroxides or metal oxides during ball mixing; the pH of the metal hydroxides in water is less than pH=10, and a solubility less than that of NaOH in water at 25° C.;

the metal oxides capable of reacting with water and hydroxide generated therefrom having a pH value in water less than pH=10;

the organometallic carboxylates have an average particle size of 10-50 microns, using

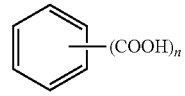

and NaOH as starting materials to prepare

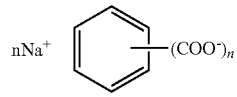

and NaOH is recycled during the reaction, and the amount of NaOH supplemented in each cycle of reaction is according to a molar ratio of

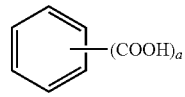

to NaOH in 1:0.05-0.2.

2. The method for preparing nano organometallic carboxylates according to claim 1, wherein the metal hydroxides comprise calcium hydroxide, magnesium hydroxide, and zinc hydroxide; the metal oxides comprise calcium oxide, magnesium oxide, and zinc oxide.

3. The method for preparing nano organometallic carboxylates according to claim 1, wherein the ball milling frequency is 30~100 Hz and time duration thereof is 120 to 300 min.

4. The method for preparing nano organometallic carboxylates according to claim 1, further comprising controlling mass concentration of NaOH during reaction at 5% to 15%.

* * * * *